United States Patent [19]

Thompson

[11] Patent Number: 5,049,137

[45] Date of Patent: Sep. 17, 1991

[54] PREPACKAGED SYRINGE AND CATHETER APPARATUS FOR DEEP ADMINISTRATION OF A FLUID, AND METHOD OF MAKING SAME

[76] Inventor: Jeffrey E. Thompson, N775 Bloomer Mill Rd., LaCrosse, Wis. 54601

[21] Appl. No.: 404,666

[22] Filed: Sep. 8, 1989

[51] Int. Cl.$^5$ ............................................. A61M 5/325
[52] U.S. Cl. ..................................... 604/240; 604/93; 604/167
[58] Field of Search ..................................... 604/28–34, 604/51–53, 49, 50, 93, 96, 118, 121, 151, 152, 181, 183, 187, 192, 193, 240, 248, 415, 167, 169

[56] References Cited

U.S. PATENT DOCUMENTS

| | | | |
|---|---|---|---|
| 3,097,646 | 7/1963 | Scislowicz | 604/167 |
| 3,543,751 | 12/1970 | Sheffer | 128/208 |
| 4,405,322 | 9/1983 | Jessup | 604/232 |
| 4,447,235 | 5/1984 | Clarke | 604/169 |
| 4,525,156 | 6/1985 | Benusa et al. | 604/28 |
| 4,671,794 | 6/1987 | Braun et al. | 604/240 |
| 4,865,583 | 9/1989 | Tu | 604/53 |

OTHER PUBLICATIONS

"Effect of Injection Site on Circulation Times During Cardiac Arrest", Charles L. Emerman, MD et al., Critical Care Medicine, vol. 16, No. 11, 1988, pp. 1138–1141.
"Intrapulmonary Epinephrine During Prolonged Cardiopulmonary Resuscitation: Improved Regional Blood Flow and Resuscitation in Dogs", Sandra H. Ralston, RN, PhD et al., Annals of Emergency Medicine, vol. 13, No. 2, Feb. 1984, pp. 79/15–86/22.
"Endotracheal Versus Intravenus Epinephrine during Electromechanical Dissociation with CPR in Dogs", Annals of Emergency Medicine, vol. 14, No. 11, Nov. 1985, pp. 1044/25–1048/29.
"Access for Drug Administration During Cardiopulmonary Resuscitation", William Kaye, MD. et al., Critical Care Medicine, vol. 16, No. 2, 1988, pp. 179–182.
"Comparison of Deep and Shallow Endotracheal Administration of Dionosil in Dogs and Effect of Manual Hyperventilation", Michael I. Greenberg, MD. et al., Annals of Emergency Medicine, vol. 14, No. 3, Mar. 1985, pp. 209/37–212/40.
"Endotracheal Drug Administration", Critical Care Clinics of North America, 1989, pp. 739–741.
Leon Chameides, M.D. et al., "Textbook of Pediatric Advanced Life Support", American Heart Association 1988, II. General Guidelines for Administering Medications, p. 48.
Mark C. Rogers, M.D., Joseph E. Parrillo, M.D., "The Year Book of Critical Care Medicine", 1989, Chap. 2, Access for Drug Admin. during Cardiopulmonary Resuscitation, Kaye W. Bircher NG.
Mark C. Rogers, M.D., "Textbook of Pediatric Intensive Care", vol. One, Chapter 2, Advanced Life Support.
Arno L. Zaritsky, M.D., "Pediatric Critical Care Clinical Review Series", Part 1, June 3–5, 1989, Pediatric CPR: Current Concepts, Lecture 1, pp. 1–2.
Ronald S. Bloom, M.D., Catherine Cropley, R.N., M.N., "Textbook of Neonatal Resuscitation", 1987 American Heart Association, Intratracheal Instillation, p. 6–6.

Primary Examiner—John D. Yasko
Assistant Examiner—Corrine Maglione
Attorney, Agent, or Firm—Andrus, Sceales, Starke & Sawall

[57] ABSTRACT

A medical apparatus for providing deep administration of a fluid into the lung of a patient comprises a prepackaged, preloaded syringe and catheter. A stopper or plug is placed at the proximal end of the catheter, and receives the needle tip therewithin. The needle is selectively movable through the plug so as to place the lumen of the needle in communication with the catheter passage, so that fluid ejected from the syringe passes through the needle and into the catheter passage after placement of the catheter within the tracheal passage of a patient. In this manner, deep administration of the fluid into the patient's lung can be accomplished. Alternatively, the needle may be withdrawn from the passage and the syringe used in a conventional manner for directly injecting fluid into the patient.

5 Claims, 1 Drawing Sheet

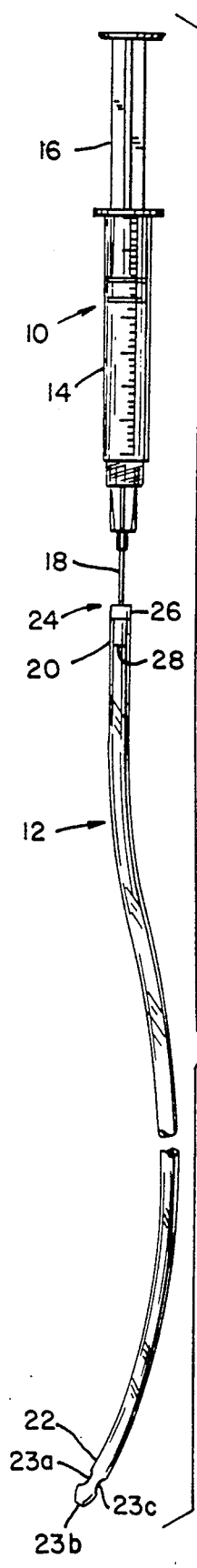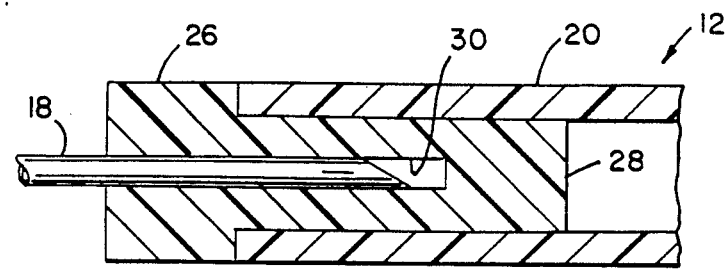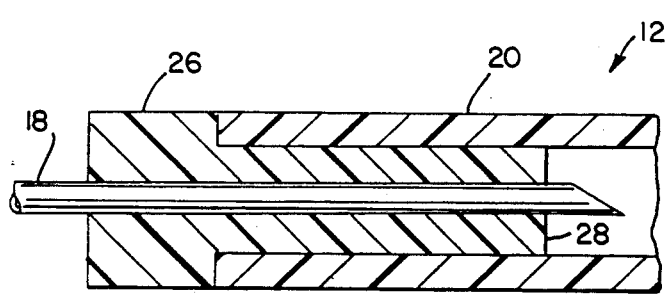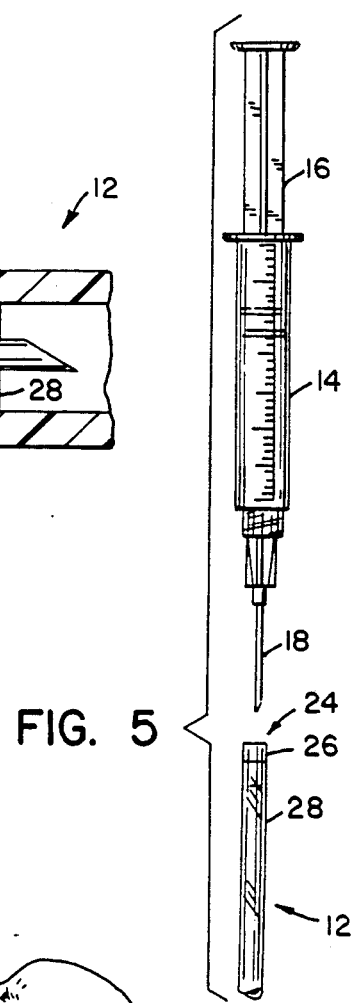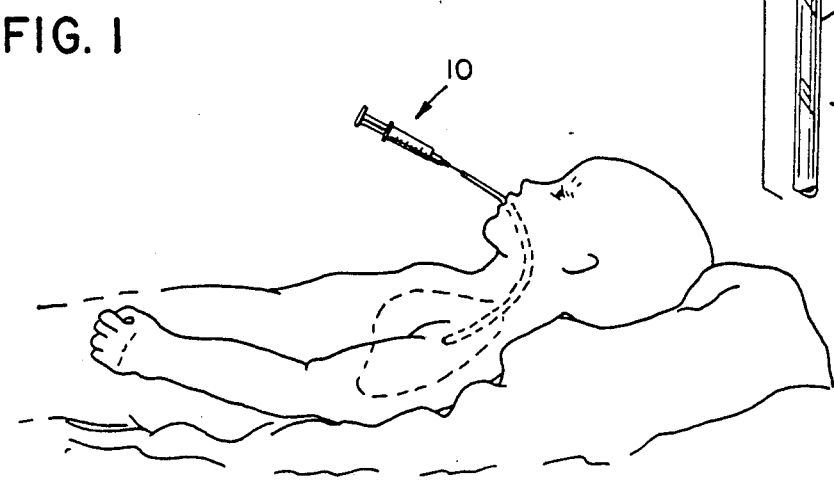
FIG. 1
FIG. 2
FIG. 3
FIG. 4
FIG. 5

PREPACKAGED SYRINGE AND CATHETER APPARATUS FOR DEEP ADMINISTRATION OF A FLUID, AND METHOD OF MAKING SAME

BACKGROUND AND SUMMARY

This invention relates to a medical apparatus, and more particularly to an apparatus for endotracheally administering a fluid to a patient, and a method for assembling such an apparatus.

It has been found that an effective method of delivering a drug, such as epinephrine, to the heart of a pulseless patient is to administer the drug at a point deep within a lung of the patient, and to thereafter perform cardiopulmonary resuscitation. Several studies have indicated that this method of drug delivery shortens circulation time of the drug and increases chances of patient survival.

In reviving a pulseless patient, time is of the essence. While currently available evidence points to advantages offered by deep drug administration, there is no commercially available apparatus for quickly facilitating deep drug administration.

A commercially available system produced by Abbot Laboratories under the Trademark ABBOJECT® provides a preloaded container of medication adapted for intravenous use with a specially-made syringe. To use this system for endotracheal administration, the components must be unpackaged and the container loaded onto the syringe. Next, a three-way stopcock or other fitting must be applied, and a feeding tube or a vascular catheter must be adapted to the system. The medication can then be injected through the catheter.

This procedure involves numerous steps and, accordingly, a certain amount of time. This invention addresses this situation, and is intended to reduce the valuable time which lapses before the drug reaches the patient's heart.

In accordance with the invention, an apparatus for deep administration of a fluid, such as epinephrine or other such drug, comprises a body including a cavity adapted to receive a quantity of fluid. A discharge opening is in communication with the cavity for discharging fluid therefrom. A predetermined quantity of fluid is placed within the cavity. User-actuated means is associated with the body for ejecting the fluid from the body cavity through the discharge opening. A flexible catheter having a passage therethrough, and having a proximal end and a distal end, is adapted for connection to the body such that the proximal end of the catheter is in communication with the cavity discharge opening. In this manner, when the user-actuated means is actuated for ejecting fluid from the cavity through the discharge opening, the fluid is received within and passes through the catheter passage. The distal end of the catheter includes an outlet for discharging the fluid from the catheter at a point substantially removed from the cavity discharge opening. The catheter is adapted for endotracheal placement within a patient, such that the outlet formed in the distal end of the catheter discharges the fluid at a point deep within the lung of the patient. In a preferred embodiment, the body comprises a hollow barrel, and the user-actuated fluid ejecting means comprises a plunger movably mounted within the hollow barrel. A needle is preferably affixed to the end of the barrel, and includes a lumen which receives fluid ejected through the discharge opening. The tip of the needle is adapted for placement within the proximal end of the catheter, and sealing means is provided for enclosing the tip of the needle and sealing the proximal end of the catheter. The sealing means is preferably a stopper or the like for placement into the catheter passage at its proximal end, with a needle-receiving passage formed in the stopper. The apparatus is preferably movable between a storage position and an operative position. In the storage position, the end of the needle is received within the passage formed in the stopper, such that the tip of the needle is isolated and is not in communication with the catheter passage. In its operative position, the tip of the needle is forced through the stopper so that the needle tip is in communication with the catheter passage. In this position, the fluid can then be ejected from the barrel and through the needle into the catheter passage for ultimate discharge through the distal end of the catheter. Alternatively, the needle can be withdrawn from the stopper and used in its normal fashion for directly injecting the fluid into the patient. For example, under less critical circumstances, a routine subcutaneous or intravenous injection could be performed to administer the drug. In a serious situation, the needle could be withdrawn from the stopper and the drug directly injected into the heart if necessary.

The invention also contemplates a method of assembling a prepackaged medical apparatus, substantially in accordance with the foregoing summary.

BRIEF DESCRIPTION OF THE DRAWINGS

The drawings illustrate the best mode presently contemplated of carrying out the invention.

In the drawings:

FIG. 1 is an elevation view of the assembled prepackaged syringe and catheter apparatus of the invention;

FIG. 2 is an enlarged partial sectional view showing the stopper placed in the proximal end of the catheter, with the needle tip placed in the needle-receiving passage formed in the stopper and in its storage position;

FIG. 3 is a view similar to FIG. 2 showing the needle moved to its operative postion;

FIG. 4 is a view showing the apparatus of the invention in use on a patient; and FIG. 5 is a partial elevation view similar to FIG. 1 showing the needle withdrawn from the needle-receiving passage formed in the stopper.

DETAILED DESCRIPTION OF THE PREFERRED EMBODIMENT

As shown in FIG. 1, a prepackaged medical apparatus for providing deep administration of a fluid generally includes a syringe 10 and a thin bore catheter 12. Syringe 10 may be of conventional construction, including a cylindrical body portion 14 provided with an internal cavity and a closed end. A perdetermined quantity of fluid, such as the drug epinephrine or the like, is placed within the cavity of the body portion 14. A plunger 16 is slidably mounted within the cavity of body 14. As is known, downward movement of plunger 16 within the cavity of body 14 ejects fluid contained within the cavity therefrom through a discharge opening formed in the closed end of body 14. A needle 18 is connected to the closed end of body 14, and includes a lumen in communication with the discharge opening formed in body 14.

Catheter 12 is formed of a flexible material, and has a proximal end 20 and a distal end 22. A passage extends throughout the length of catheter 12, and a series of discharge openings 23a, 23b and 23c are formed in distal end 22. As is known, catheter 12 is formed of a flexible material.

A stopper 24, which includes an enlarged head portion 26 and a body portion 28, is adapted for placement within proximal end 20 of catheter 12. As shown in FIGS. 2 and 3, body portion 28 is received within the passage in catheter 12 so as to seal proximal end 20.

A longitudinally extending and tight fitting passage 30 is formed in stopper 24, extending through head portion 26 and partially through body portion 28. Passage 30 is adapted to receive the end of needle 18. As shown in FIGS. 2 and 3, needle 18 is movable within passage 30 between an inoperative, or storage, position as shown in FIG. 2, and an operative postion as shown in FIG. 3. In the position as shown in FIG. 2, the sharpened tip of needle 18 is retained within passage 30, so that communication between the passage of catheter 12 and the lumen of needle 18 is cut off. In the position as shown in FIG. 3, needle 18 is forced through head portion 28 so that its sharpened tip is disposed within the passage in catheter 12 and communication between the lumen of needle 18 and catheter 12 is established.

In operation, the apparatus of the invention functions as follows. Catheter 12 is inserted into the endotracheal tract of the patient as shown in FIG. 4, or through an endotracheal tube already in place in the patient, so that its distal end 22 is placed deep within the patient's lung. Either before or after placement of the catheter, needle 18 of syringe 10 is moved to its operative position as shown in FIG. 3, so that communication between the lumen of needle 18 and the passage of catheter 12 is established. Thereafter, the user actuates plunger 16 so as to eject medication from the cavity formed in syringe body portion 14. The ejected medication flows from the discharge opening of body portion 14, through the lumen of needle 18 and into the passage formed in catheter 12. The medication flows through catheter 12 and is discharged at discharge openings 23a–23c formed therein at distal end 22 for administration to the lung area of the patient. In accordance with known medical practice, cardiopulmonary resuscitation is then performed on the patient so as to ultimately deliver the drug to the patient's heart.

Referring to FIG. 5, it is seen that needle 18 of syringe 10 may be removed from stopper 24 prior to ejection of the fluid from syringe body portion 14. In this manner, the pre-loaded syringe 10 may be used in a conventional manner for directly injecting the fluid into the patient.

Various alternatives and embodiments are contemplated as being within the scope of the following claims particularly pointing out and distinctly claiming the subject matter regarded as the invention.

I claim:

1. An apparatus for deep administration of a fluid, comprising in combination:
   a body including a cavity and having a discharge opening;
   a predetermined quantity of fluid placed within said cavity;
   user-actuated means associated with said body for ejecting the fluid from said cavity through said discharge opening;
   a needle connected to said body and having a lumen in communication with the discharge opening of said body cavity to receive fluid ejected therefrom;
   a flexible catheter interconnected with said needle and including a passage and having a proximal end and a distal end, with the distal end of said catheter being adapted for placement within a body passage of a patient and including an outlet;
   a stopper member connected to the proximal end of said catheter and having a passage extending partially therethrough within which the end of said needle is received, wherein the stopper member cuts off communication between the passage of said catheter and the lumen of said needle when the end of said needle is received within said stopper member passage; and
   wherein the end of said needle is removable from said stopper member for allowing direct injection of fluid through said needle into said patient, and is movable through said stopper member to place the lumen of said needle into communication with the passage of said catheter to allow deep administration of said fluid into said patient through the outlet of said catheter.

2. The apparatus of claim 1, wherein said body comprises a hollow barrel and said user-actuated fluid ejecting means comprises a plunger movably mounted within said hollow barrel.

3. The apparatus of claim 1, wherein said needle is movable within said stopper passage between a storage position in which communication between the lumen of said needle and the catheter passage is cut off, and an operative position in which communication between the lumen of said needle and said catheter passage is established, and further comprising means for retaining said needle in its storage position prior to use to prevent accidental discharge of fluid therefrom.

4. An apparatus for deep administration of a fluid, comprising:
   a body having an internal cavity adapted to receive a quantity of fluid, and a discharge opening in communication with said cavity, wherein fluid received within said cavity is adapted to be ejected therefrom by operation of a user-actuated fluid ejection mechanism;
   a needle connected to said body and having a lumen in communication with the discharge opening of said body cavity to receive fluid ejected therefrom;
   a flexible catheter interconnected with said needle and including a passage and having a proximal end and a distal end, with the distal end of the catheter having an outlet and being adapted for placement within a body passage of a patient; and
   a stopper member connected to the proximal end of said catheter and having a passage extending partially therethrough within which the end of said needle is received, wherein the stopper member cuts off communication between the passage of said catheter and the lumen of said needle when the end of said needle is received within said stopper member passage;
   wherein the end of said needle is removable from said stopper member for allowing direct injection of fluid through said needle into said patient, and is movable through said stopper member to place the lumen of said needle into communication with the passage of said catheter to allow deep administration of said fluid into said patient through the outlet of said catheter.

5. A method of assembling a medical apparatus, comprising the steps of:

providing a body having a cavity adapted to receive a quantity of fluid, said body having a discharge opening in communication with said cavity;

affixing a needle having a lumen to said body such that the lumen of said needle is in communication with said cavity discharge opening;

mounting a user-actuated ejector means to said body for ejecting fluid from said body cavity through said discharge opening and into the lumen of said needle;

providing a flexible catheter including a passage and having a proximal end with an inlet and a distal end with an outlet;

mounting a stopper in the proximal end of said catheter, said stopper having a passage formed therein adapted to receive and enclose the end of said needle; and placing the end of said needle into the passage in said stopper such that a portion of said stopper cuts off communication between the lumen of said needle and said catheter passage, wherein said needle is removable from the passage in said stopper to allow direct injection of said fluid through said needle into said patient, and is movable through said stopper for placing the lumen of said needle into communication with said catheter passage to allow deep administration of said fluid through the outlet of said catheter.

* * * * *